United States Patent [19]

Siconolfi

[11] Patent Number: 6,125,297
[45] Date of Patent: Sep. 26, 2000

[54] BODY FLUIDS MONITOR

[75] Inventor: Steven F. Siconolfi, Grosse Pointe Pk., Mich.

[73] Assignee: The United States of America as represented by the United States National Aeronautics and Space Administration, Washington, D.C.

[21] Appl. No.: 09/035,413

[22] Filed: Feb. 6, 1998

[51] Int. Cl.$^7$ ............................................. A61B 5/05
[52] U.S. Cl. ........................................ 600/547; 600/484
[58] Field of Search ........................... 600/547, 546, 600/484

[56] References Cited

U.S. PATENT DOCUMENTS

| | | | |
|---|---|---|---|
| 4,793,362 | 12/1988 | Tedner | 128/734 |
| 4,895,163 | 1/1990 | Libke et al. | 128/734 |
| 4,911,175 | 3/1990 | Shizgal | 128/734 |
| 5,063,937 | 11/1991 | Ezenwa et al. | 128/723 |
| 5,086,781 | 2/1992 | Bookspan | 128/734 |
| 5,280,429 | 1/1994 | Withers | 364/413.15 |
| 5,335,667 | 8/1994 | Cha et al. | 128/734 |
| 5,449,000 | 9/1995 | Libke et al. | 128/734 |
| 5,746,214 | 5/1998 | Brown et al. | 128/693 |
| 5,807,272 | 9/1998 | Kun et al. | 600/547 |

OTHER PUBLICATIONS

"Estimation of Body Fluid Volumes Using Tetrapolar Bio-electrical Impedance Measurements" H. Lukaski and W. Bolonchuk; Aviation, Space, and Environmental Medicine; pp 1163–1169; Dec. 1988.

"Estimation of Total Body Water by Bioelectrical Impedance Analysis" R. Kushner and D. Schoeller; The American Journal of Clinical Nutrition; pp 417–424; Sep. 1986.

"Estimation of Extracellular and Total Body Water by Multiple–Frequency Bioelectrical–Impedance Measurement" K. Segal, S. Burastero, A. Chun, P. Coronel, R. Pierson, and J. Wang; The American Journal of Clinical Nutrition; pp 26–29; 1991.

"Determining Blood and Plasma Volumes Using Bioelectrical Response Spectroscopy" S. Siconolfi, M. Nusynowitz, S. Suire, A. Moore, and J. Leig; Medicine and Science in Sports and Exercise; pp 1510–1516; Aug. 1996.

"Assessing Total Body and Extracellular Water from Bio-electrical Response Spectroscopy" S. Siconolfi, R. Gretebeck, W. Wong, R. Pietrzyk, and S. Suire; J. Appl. Physiol. (82)2); pp 704–710; 1997.

"Assessing Total Blood (TBV), Plasma Volume (PV), ATBV, and APV from Bioelectrical Response Spectroscopy (BERS)" S. Siconolfi, M. Nusynowitz, S. Suire, A. Moore, and A. Rogers; FASEB J. 1994; vol. 8(4), A15.

"The Effects of Body Fluid Shifts on Single and Multi–Frequency Bioelectrical Analyses" S. Siconolfi and R. Gretebeck; Medicine and Science in Sports and Exercise; 26(5):S202, 1994.

*Primary Examiner*—Marvin M. Lateef
*Assistant Examiner*—Eleni Mantis Mercader
*Attorney, Agent, or Firm*—James M. Cate

[57] ABSTRACT

Method and apparatus are described for determining volumes of body fluids in a subject using bioelectrical response spectroscopy. The human body is represented using an electrical circuit. Intra-cellular water is represented by a resistor in series with a capacitor; extra-cellular water is represented by a resistor in series with two parallel inductors. The parallel inductors represent the resistance due to vascular fluids. An alternating, low amperage, multi-frequency signal is applied to determine a subject's impedance and resistance. From these data, statistical regression is used to determine a 1% impedance where the subject's impedance changes by no more than 1% over a 25 kHz interval. Circuit components of the human body circuit are determined based on the 1% impedance. Equations for calculating total body water, extra-cellular water, total blood volume, and plasma volume are developed based on the circuit components.

39 Claims, 10 Drawing Sheets

BODY FLUIDS MONITOR

ORIGIN OF THE INVENTION

The invention described herein was made by employee(s) of the United States Government and may be manufactured and used by or for the Government of the United States of America for governmental purposes without the payment of any royalties thereon or therefor.

BACKGROUND OF THE INVENTION

The invention relates to a process for determining amounts of body fluids in a subject using bioelectrical response spectroscopy (BRS).

Determining amounts of body fluids in a subject and detecting changes in the level of fluids is an important clinical and research tool. For example, it is documented that athletes show decreases in plasma volume after they stop exercise training. Similarly, exposure to real or simulated micro gravity may decrease plasma or blood volume in astronauts. This decrease may affect the physical performance and safety of the astronauts during space flights. Being able to assess blood or plasma volumes during flight may help evaluate the effectiveness of measures designed to restore or maintain those volumes.

Prior art FIG. 1 shows a typical BRS method for determining volumes of body fluids in a subject. A signal generator 1 applies an alternating, low amperage signal through electrodes 2 to a subject 3. The alternating, low amperage signal travels through the subject 3 and is measured by an impedance analyzer 4 to determine a subject's impedance and resistance. The impedance and resistance are used to determine the subject's volumes of body fluids.

One known BRS method assumed that total body resistance was due to a total body water and was equivalent to the resistance of a wire. The volume of the wire is proportional to the resistance of the wire and directly related to the square of the length of the wire and the resistivity of the wire:

$$\text{volume} = \rho \cdot \text{length}^2 / R$$

where $\rho$ is the specific resistivity (ohms·cm) of the wire and R is the resistance. Using this electrical law and statistical regression, these investigators were able to develop estimation equations for total body water.

One known BRS method treated the body as a plurality of segmented conductors having uniform cross-sectional area. By measuring impedance to determine the composition of one or more body segments, a total body composition could be determined.

One known BRS method found that input signals of different frequencies would produce different resistances. These resistances were thought to be specific to different fluid compartments (e.g. extra-cellular fluid) and not to total body water.

One know BRS method used input signals of multiple frequencies to determine volumes of body fluids. These investigators used a Cole-Cole plot and iterative curve fitting techniques to determine extra-cellular and total body resistance.

One known BRS method assumed that capacitance was present in the body. This was based on a theory that cell membranes in the body acted like capacitors. Prior art FIG. 2 shows an electric circuit model of a human body that contains a capacitor. A series combination of resistor $R_I$ and capacitor C represented an intra-cellular impedance. A single resistor $R_E$ represented an extra-cellular resistance. The intra-cellular and extra-cellular branches were parallel to each other. A total impedance of the circuit between terminals 5 and 6 represented a total body impedance $Z_T$ that was thought to be due to a total body water.

One known BRS method assumed that inductance was also present in the body. This was based on a theory that vascular fluids in the body acted like an inductor. Prior art FIG. 3 shows a circuit model of the human body that included an inductor. A series combination of resistor $R_I$ and capacitor C represented an intra-cellular impedance. A series combination of resistor $R_E$ and inductor $L_E$ represented an extra-cellular impedance. The intra-cellular and extra-cellular branches were parallel to each other. A total impedance of the circuit between terminals 7 and 8 represented a total body impedance $Z_T$. This model showed an 11% shift in blood volume after subjects completed 40 minutes of supine rest while resistance and estimates of total body water changed only 0.4–1.5%. These data suggested that the change in inductance, not resistance, may relate to known increase in blood volume (~10%) that occurs with supine rest.

Other known methods determined volumes of body fluids using dilution techniques that required injecting isotopic tracers into the subject's body. $^{51}$Cr-labeled hematocrit, $^{125}$I-labeled albumin, carbon monoxide, and inert dyes (e.g. Evans Blue) are examples of tracers used to assess blood, red cell, or plasma volumes. Most of these methods required multiple blood samples and sufficient time for the tracers to equilibrate within the vascular compartment. Also, repeat assessments must wait until the level of tracer in the blood decreased.

SUMMARY OF THE INVENTION

In some embodiments, the invention relates to a process for determining a volume of body fluid in a subject, comprising the steps of applying a signal to a subject, increasing the frequency of the signal by predetemined increments, measuring an impedance and a resistance of the subject at each frequency increment, determining a total body frequency $F_T$, wherein the total body frequency $F_T$ is the frequency at which the impedance decreases by a predefined percent over a predefined frequency interval, determining circuit components of a human body circuit model, wherein the circuit components comprise a total body impedance $Z_T$, a total body resistance $R_T$, an extra-cellular resistance $R_E$, an intra-cellular resistance $R_I$, a capacitance C, a self-inductance L, and a mutual-inductance M, and determining the volume of body fluid from the circuit components.

In some embodiments, the invention relates to an apparatus for determining a volume of body fluid in a subject, comprising of means for applying a signal to a subject, means for increasing a frequency of the signal by predetermined increments, means for measuring an impedance and a resistance of the subject at each frequency increment, means for determining a total body frequency $F_T$, wherein the total body frequency $F_T$ is the frequency at which the impedance decreases by a predefined percent over a predefined frequency interval, means for determining circuit components of a human body circuit model, wherein the circuit components comprise a total body impedance $Z_T$, a total body resistance $R_T$, an extra-cellular resistance $R_E$, an intra-cellular resistance $R_I$, a capacitance C, a self-inductance L, and a mutual-inductance M, and means for determining the volume of body fluid from the circuit components.

In some embodiments, the invention relates to an apparatus for determining a volume of body fluid in a subject, comprising of a signal generator configured to apply a signal to a subject and increase a frequency of the signal by predetermined increments, an impedance analyzer configured to measure an impedance and a resistance of the subject at each frequency increment, and a data processing unit configured to determine a total body frequency $F_T$ where the impedance decreases by a predefined percent over a predefined frequency interval, determine circuit components of a human body circuit model including a total body impedance $Z_T$, a total body resistance $R_T$, an extra-cellular resistance $R_E$, an intra-cellular resistance $R_I$, a capacitance C, a self-inductance L, and a mutual-inductance M, and determine the volume of body fluid from the circuit components.

Advantages of the invention include one or more of the following: a fast, repeatable, non-invasive, and non-radioacive method for determining a volume of body fluid in a subject; and an accurate electrical circuit representation of the human body. Other advantages and features will become apparent from the following description and from the claims.

DESCRIPTION OF THE PREFERRED EMBODIMENTS

Preferred embodiments will now be described with reference to FIGS. 4–13.

Figure 1:
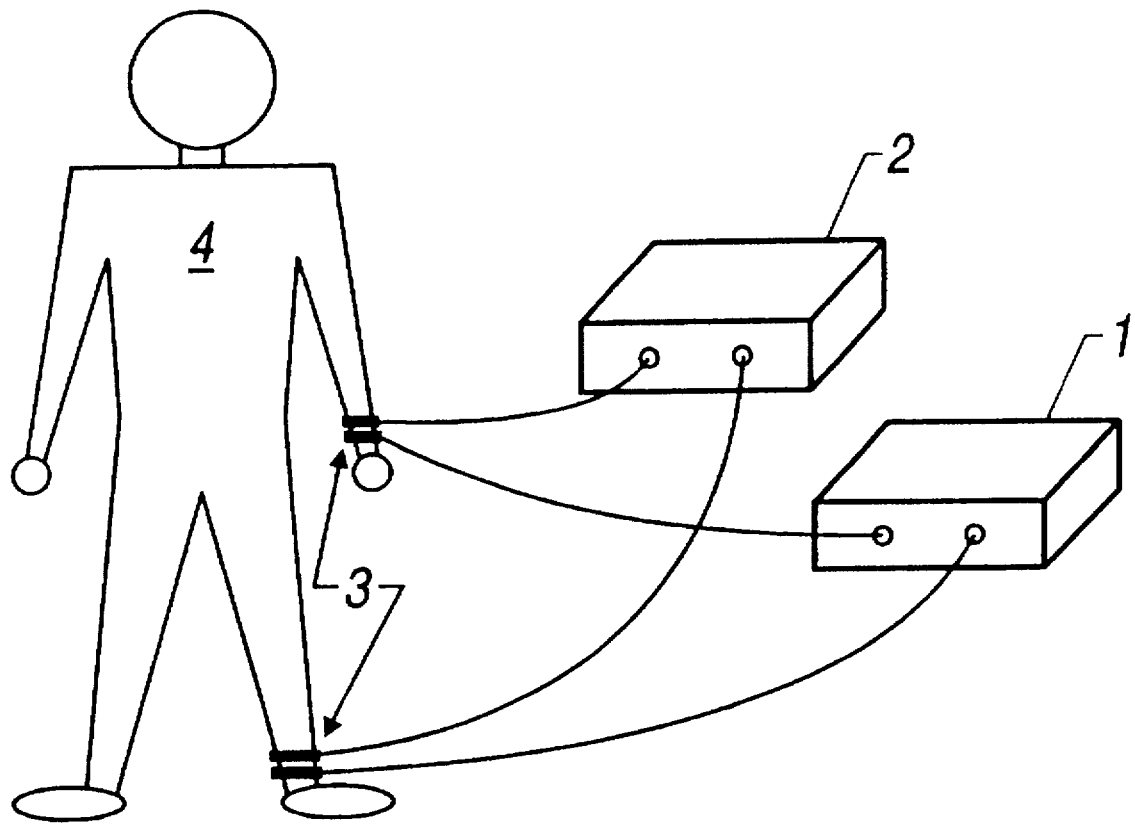
FIG. 1 illustrates a prior art BRS method for determining volumes of body fluids in a subject.
Figure 2:
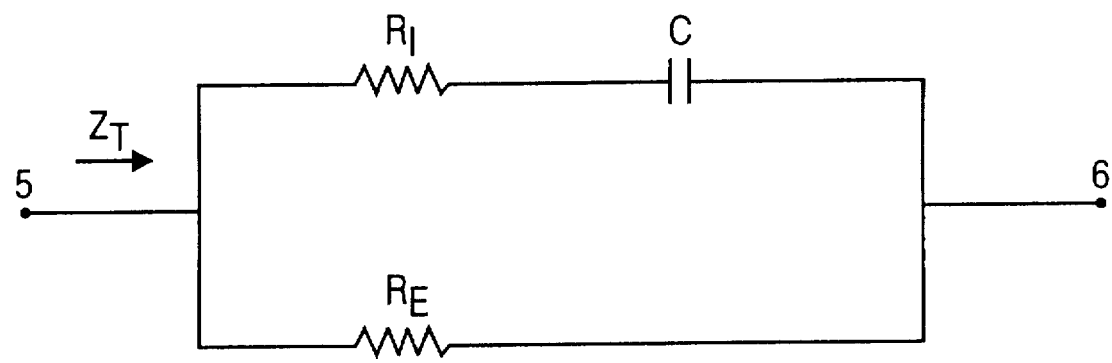
FIG. 2 illustrates a prior art electrical circuit model of a human body containing a capacitor.
Figure 3:
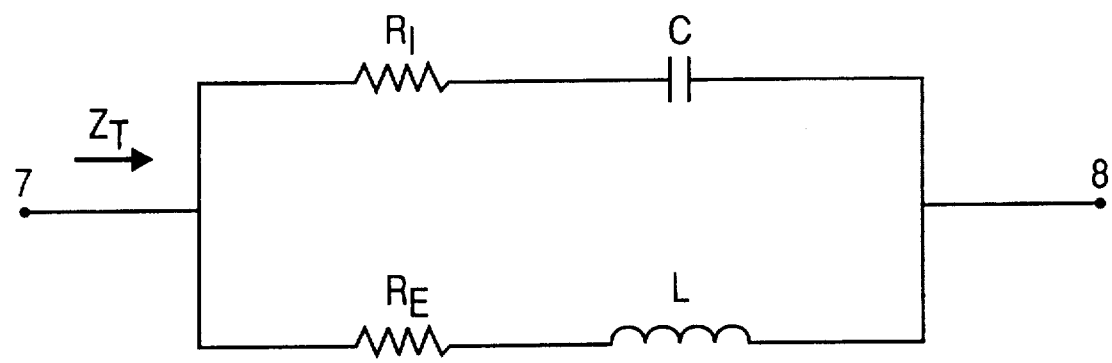
FIG. 3 illustrates a prior art electrical circuit model of a human body containing an inductor.
Figure 4:
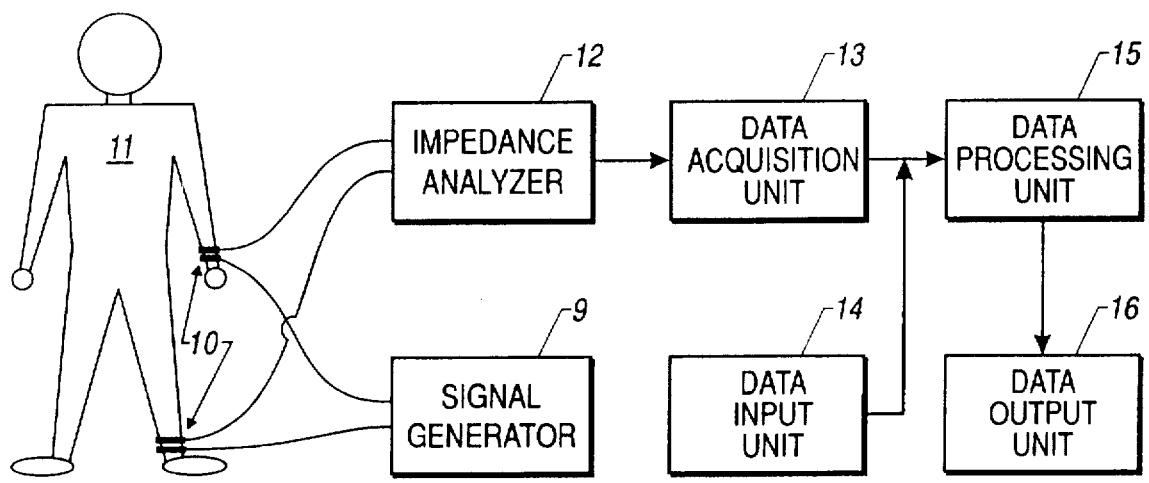
FIG. 4 illustrates a block diagram according to one embodiment of the present invention.

Referring to FIG. 4, a block diagram shows a system for determining volumes of body fluids in a subject. A signal generator 9 generates an alternating, low amperage signal, which may be a square wave of about 250 uA amplitude. The signal generator 9 is connected to the subject by electrodes 10 which are attached to distal portions of a subject 11, e.g. ventral surface of the hand and end of the foot. The electrodes 10 may be Ag/AgCl pre-gelled electrodes such as those available from Classical Medical Products, Inc., Muskego, Wis. The signal generator 9 also increases the frequency of the signal, which may be from 0 to 300 kHz, by predetermined increments. The predetermined increments may include, but are not limited to, 5, 50, 67, 85, 100, 150, 166, 200, 250, and 300 kHz. An impedance analyzer 12 measures an impedance and a resistance of the subject 11 at each frequency increment. Frequencies above 300 kHz were not used because changes in impedance or resistance at those frequencies were due to "skin effect" and did not represent penetration of fluid compartments. The impedance analyzer 12 is connected to the subject 11 by electrodes 10 that are attached to distal portions of the subject 11, e.g. the upper wrist and ventral surface of the foot. The signal generator 9 and impedance analyzer 12 may be, for example, a Hewlett Packard Model 4284A Precision LCR Meter. The Hewlett Packard Model 4284A Precision LCR Meter uses an auto-balancing bridge technique to assess impedance and phase, and is therefore suitable for human application so long as the electrodes 10 have a mutual ground and the meter is optically isolated from the AC source. Comparisons between the HP impedance meter, a Valhalla meter (Scientific Incorporated, Valhalla, Calif.) and a Xitron Model 4000B meter (Xitron Technologies, San Diego, Calif.) using standardized subjects showed equivalence for resistance (±1 ohms) during near simultaneous measurements. A data acquisition unit 13, which may be a computer, acquires and stores the impedance and resistance for processing. A data input unit 14, which may be a keyboard, allows manual entry of the subject's physical and anthropometric data into the data processing unit 15 for processing. The data processing unit 15, which may also be a computer, is configured to process the impedance and resistance and the physical and anthropometric data to determine volumes of body fluids, including an amount of total body water TBW, an amount of extra-cellular water ECW, a total blood volume TBV, and a plasma volume PV. The total body water TBW, extra-cellular water ECW, total blood volume TBV, and plasma volume PV can be determined by solving step-wise multiple regression equations that have been developed for each quantity. The results are viewed or displayed via a data output unit 16.

Figure 5:
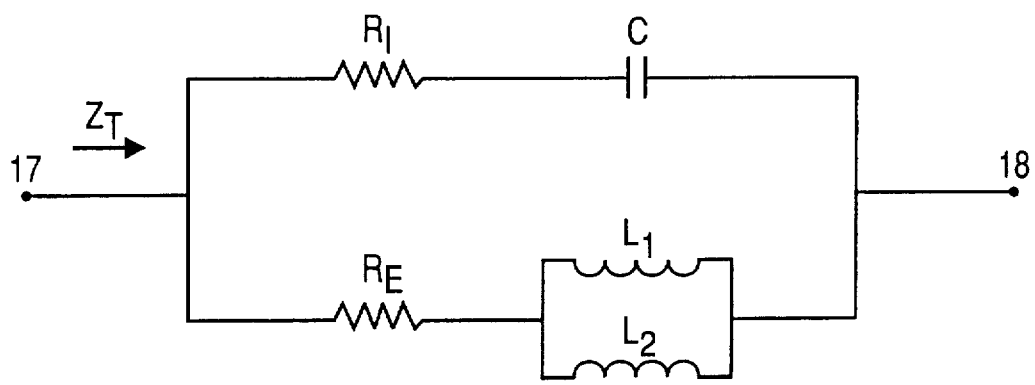
FIG. 5 illustrates an electrical circuit model of a human body according to one embodiment of the present invention.

Referring to FIG. 5, an electrical circuit model of a human body according to one embodiment of the present invention is shown. A series combination of resistor $R_I$ and capacitor C represents an intra-cellular impedance. A series combination of resistor $R_E$ and parallel inductors $L_1$ and $L_2$ represents an extra-cellular impedance. The intra-cellular and extra-cellular branches are in parallel to each other. The total impedance between terminals 15 and 16 represents a total body impedance $Z_T$. Parallel inductors $L_1$ and $L_2$ were added to the extra-cellular branch to represent vascular fluids in the body. The vascular tree has many branches that are interwoven, similar to the windings or coils of an inductor. Electrical current flowing within these branches produces an inductance called self-inductance L that must be comprehended in the human body circuit model. The vascular tree also has two main branches, arterial and venous, in which fluids flow in basically opposite directions. These two main branches act like two parallel inductors to produce an inductance called mutual-inductance M that must also be comprehended in the human body circuit model. The opposite direction of flow in the arterial and venous branches makes the mutual inductance M negative. Inductors L1 and L2 represent the self- and negative mutual-inductance.

Figure 6:
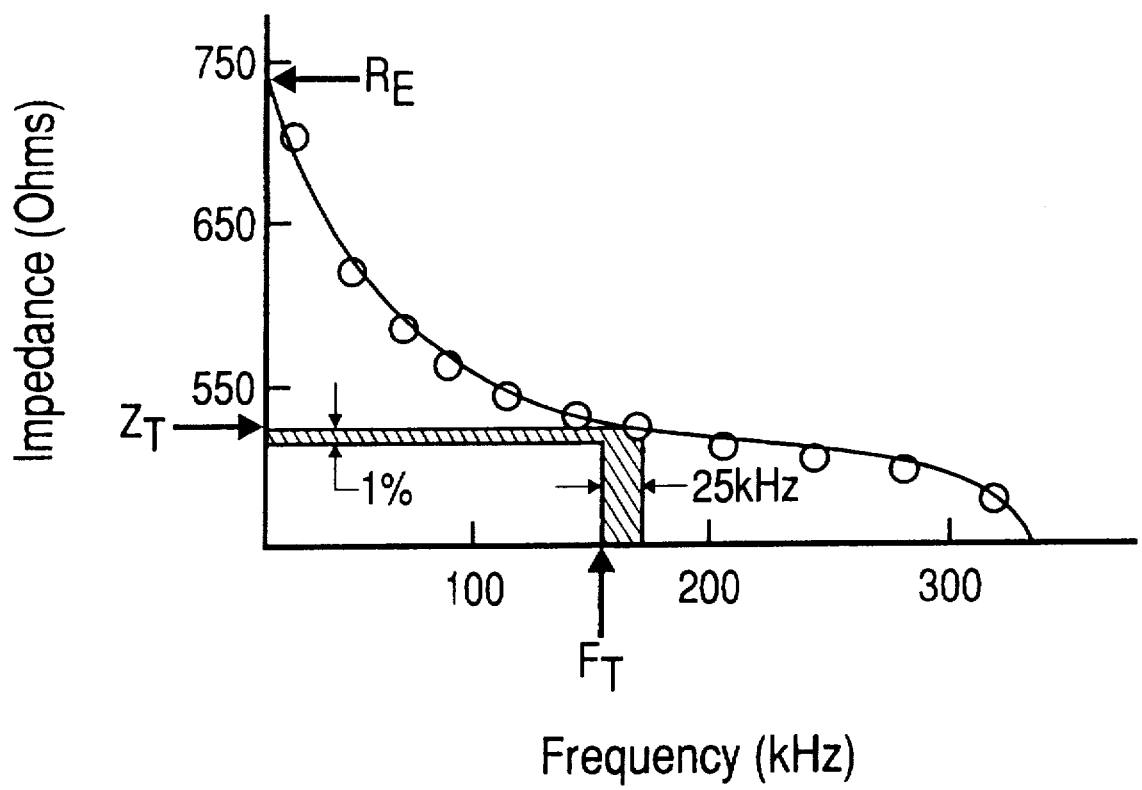
FIG. 6 illustrates a graph showing impedance versus frequency.

Referring to FIG. 6, a graph of impedance versus frequency is shown. Impedance is seen to decrease as frequency increases. However, at a certain frequency, the impedance is seen to decrease by no more than 1% over a 25 kHz increase in frequency. This 1% frequency is a total body frequency $F_T$, and the 1% impedance is a total body impedance $Z_T$. The total body impedance $Z_T$ is theoretically related to a true total body water TBW. An extra-cellular resistance $R_E$ is the resistance which corresponds to a frequency of 0 kHz.

The total body frequency $F_T$, total body impedance $Z_T$, total body resistance $R_T$, extra-cellular resistance $R_E$, intra-cellular resistance $R_I$, self-inductance L, mutual-inductance M, and capacitance $C_I$ can be determined as follows:

(1) Determine a 3rd order polynomial regression equation for impedance (ordinate) versus frequency (abscissa) in Hertz using statistical regression methods known to those skilled in the art, i.e.

$$y=\beta_0+\beta_1 \cdot x+\beta_2 \cdot x^2+\beta_3 \cdot x^3.$$

(2) Repeat (1) for resistance versus frequency.

(3) Determine the total body frequency $F_T$ by solving the following equations in order:

$$p=(0.01 \cdot \beta_2+7.5E4 \cdot \beta_3)/(0.01 \cdot \beta_3);$$

$$q=(1.875E9 \cdot \beta_3+5E4 \cdot \beta_2+0.01 \cdot \beta_1)/(0.01 \cdot \beta_3);$$

$$r=(0.01 \cdot \beta_0+1.5625E13 \cdot \beta_3+6.25E8 \cdot \beta_2+2.54E4 \cdot \beta_0)/(0.01 \cdot \beta_3);$$

$$a=(3 \cdot q-p^2)/3;$$

$$b=(2 \cdot p^3-9 \cdot q \cdot p+27 \cdot r)/27;$$

$$m=2 \cdot SQRT(-a/3);$$

$$\emptyset=(a \cos(3 \cdot b/a \cdot m))/3;$$

$$y=m \cdot \cos(\emptyset); \text{ and}$$

$$F_T=m \cdot \cos(\emptyset+4 \cdot \pi/3)-p/3.$$

(4) Determine a total reactance $X_1$ at $F_T$, $X_2$ at $F_T+25$ kHz, and $X_3$ at $F_T+50$ kHz by solving the following equation:

$$X=SQRT(Z^2-R^2)$$

where Z=impedance at the specified frequency and R=resistance at the specified frequency. To find Z and R solve the 3rd order polynomial regression equations for impedance and resistance respectively using the specified frequencies.

(5) Determine a radian frequency $\omega_1$ at $F_T$, $\omega_2$ at $F_T+25$ kHz, $\omega_3$ at and $F_T+50$ kHz by solving the following equation:

$$\omega=2 \cdot \pi \cdot \text{frequency in Hz}.$$

(6) Determine a numerical constant K by solving the following equation:

$$K=(X_2-(\omega_1 \cdot X_1/X_2))/(\omega_1^2/\omega_2-\omega_2).$$

(7) Determine the self-inductance L by solving the following equation:

$$L=-(X_3 \cdot \omega/(2 \cdot \omega_1^2))-(\omega_3^2 \cdot K/(2 \cdot \omega_1^2))-(K/2)-(X_1/(2 \cdot \omega_1)).$$

(8) Determine the mutual-inductance M by solving the following equation:

$$M=K+L$$

(9) Determine the capacitance C by solving the following equation:

$$C=1/((L \cdot \omega_1^2)-(M \cdot \omega_1^2)-(X1 \cdot \omega_1))$$

(10) Determine the total body resistance $R_T$ by using $F_T$ in Hz to solve the 3rd order polynomial regression equation for resistance in (2).

(11) Determine the extra-cellular $R_E$ by using a frequency of 0 Hz to solve the 3rd order polynomial regression equation for resistance in (2).

(12) Determine the intra-cellular resistance $R_I$ by solving the following:

$$R_I=1/((1/R_T)-(1/R_E)).$$

Figure 7A:
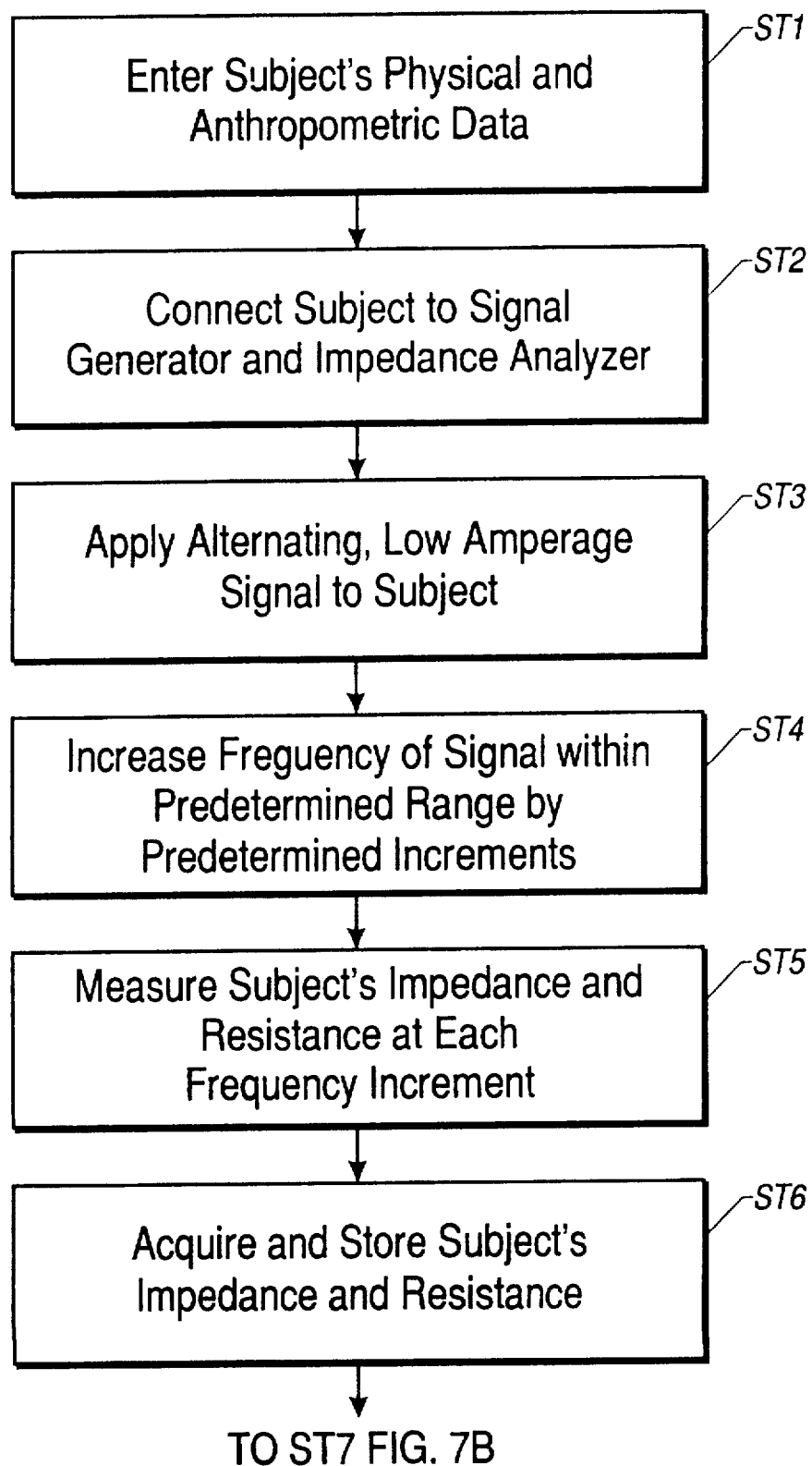
FIG. 7 illustrates a flow chart of a process for determining volumes of body fluids in a subject according to the embodiment of FIG. 4.
Figure 7B:
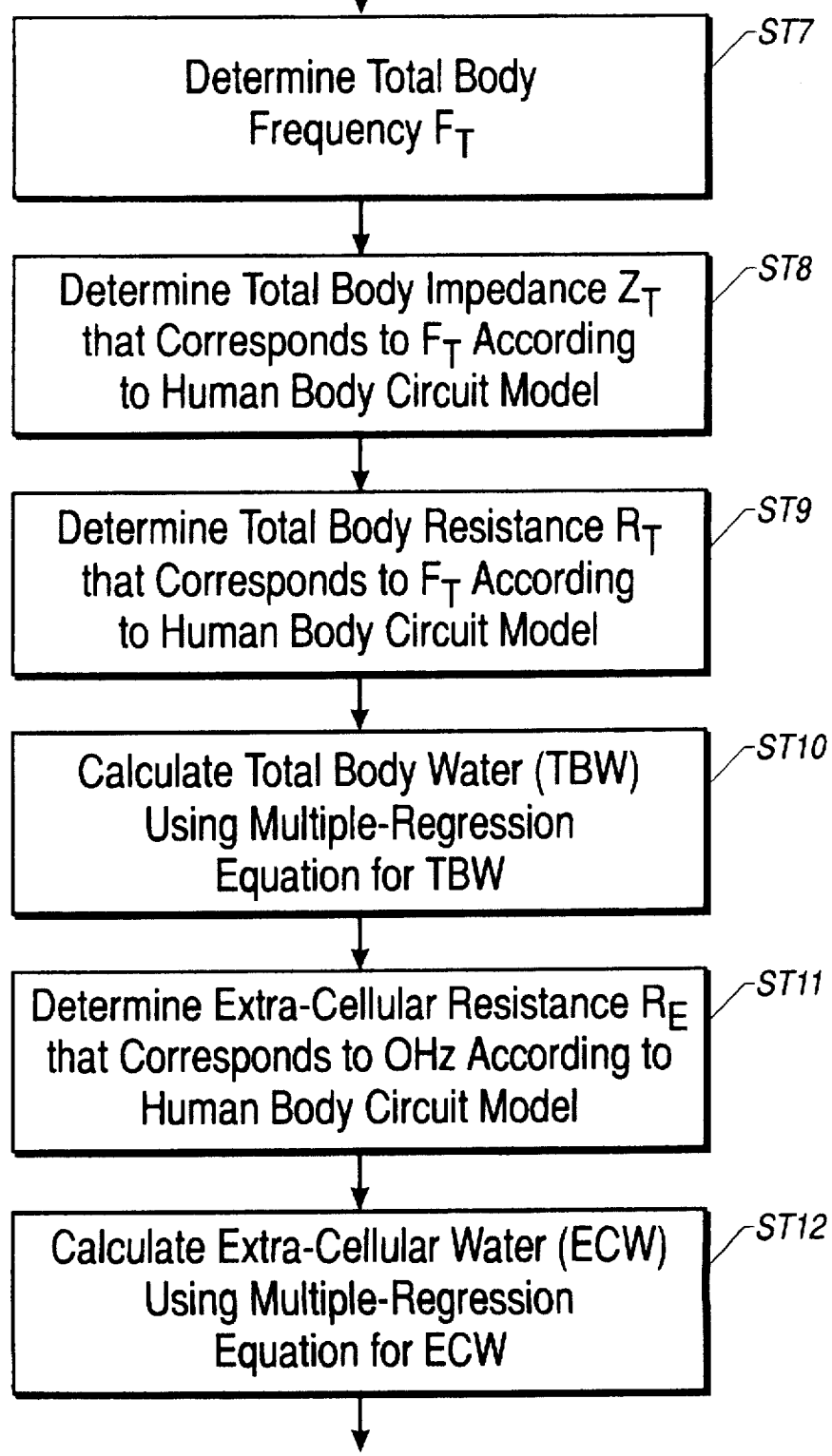
Figure 7C:
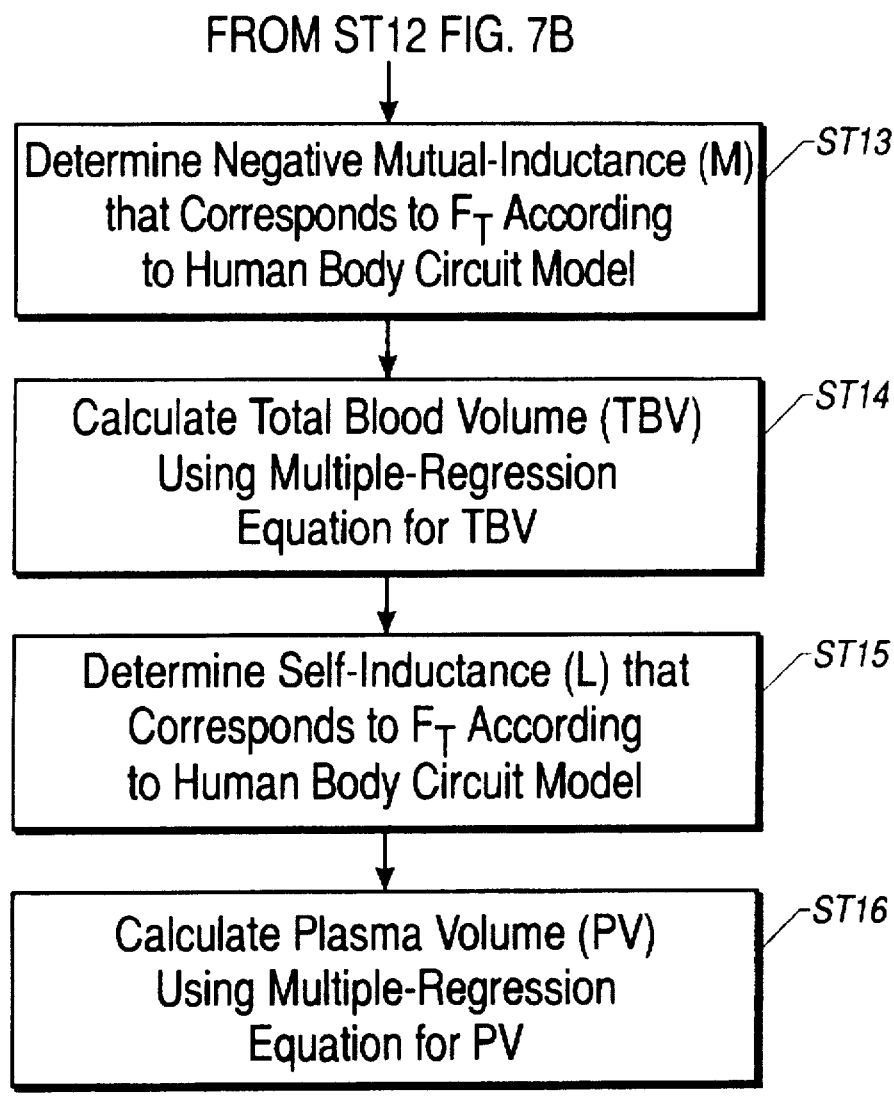

Referring to FIG. 7, the flow chart shown is a process for determining volumes of body fluids in a subject according to the embodiment of FIG. 4. In ST1, the subject's physical and anthropometric data is entered. In ST2, the subject is connected to a signal generator and an impedance analyzer. In ST3, an alternating, low amperage signal is applied to the subject. In ST4, the frequency of the alternating, low amperage signal is increased within a predetermined range, which may be from 0 to 300 kHz, by predetermined increments, which may include 5, 50, 67, 85, 100, 150, 166, 200, 250, and 300 kHz. In ST5, a subject's impedance and resistance are measured at each frequency increment. In ST6, the subject's impedance and resistance are acquired and stored. In ST7, a total body frequency $F_T$ is determined. In ST8, a total body impedance $Z_T$ that corresponds to the total body frequency $F_T$ is determined according to a human body circuit. In ST9, a total body resistance $R_T$ that corresponds to the total body frequency $F_T$ is determined according to the human body circuit. In ST10, a total body water TBW is calculated using the step-wise multiple regression equation for TBW. In ST11, an extra-cellular resistance $R_E$ that corresponds to a frequency of 0 Hz is determined according to the human body circuit. In ST12, an extra-cellular water ECW is calculated using the step-wise multiple regression equation for ECW. In ST13, a mutual-inductance M that corresponds to the total body frequency $F_T$ is determined according to the human body circuit. In ST14, a total blood volume TBV is calculated using the step-wise multiple regression equation for TBV. In ST15, a self-inductance L that corresponds to the total body frequency $F_T$ is determined according to the human body circuit. In ST16, a total plasma volume PV is calculated using the step-wise multiple regression equation for PV.

The equations for calculating total body water TBW, extra-cellular water ECW, total blood volume TBV, and plasma volume PV were developed using step-wise multiple regression of impedance, resistance, and body fluids data obtained in laboratory studies.

Two studies were conducted: one to determine TBW and ECW, the other to determine TBV and PV. All subjects who participated in the studies passed an Air Force Class III physical and were divided randomly into two groups, a development group and a validity group. For subjects in the development group, impedance and resistance were obtained using the embodiment of FIG. 4, and TBW, ECW, TBV, and PV were obtained using dilution. These data were used in step-wise multiple regression to develop equations to predict TBW, ECW, TBV, and PV. For subjects in the validity group, TBW, ECW, TBV, and PV were obtained using dilution. The equations developed using subjects in the development group were applied to subjects in the validity group, and the results thereof were compared to the results obtained using dilution.

In the study to develop the equations to calculate total body water TBW and extra-cellular water ECW the following subjects participated: 23 subjects in the TBW development group and 31 subjects in the TBW validity group; 17 subjects in the ECW development group and 9 subjects in the ECW validity group. Table 1 shows the characteristics of the subjects.

TABLE 1

TBW and ECW Subject Characteristics

| | Development Group | | Validity Group | |
|---|---|---|---|---|
| | TBW | ECW | TBW | ECW |
| Age, yr | 32.0 ± 6.6 | 33.8 ± 5.8 | 35 ± 6.4 | 34.0 ± 7.0 |
| Height, cm | 168 ± 6 | 170 ± 11 | 170 ± 10 | 170 ± 9 |
| Mass, kg | 67.8 ± 13.0 | 64.7 ± 11.4 | 69.2 ± 14.0 | 72.9 ± 17.1 |
| TBW, kg | 38.8 ± 7.7 | 34.6 ± 6.3 | 36.8 ± 7.8 | 38.6 ± 9.6 |
| ECW, kg | N/A | 15.4 ± 2.9 | 16.0 ± 3.4 | 16.2 ± 3.8 |
| Sex | 10M/13F | 6M/11F | 16M/15F | 6M/3F |

The subjects in the TBW development group had their TBW evaluated with $^{18}$O-labeled water. The subjects in the TBW validity group were evaluated with deuterium oxide ($^2$H$_2$O). The unavailability of $^{18}$O-labeled water and the desire to demonstrate the robust nature of the present invention led to the use ($^2$H$_2$O) for the validity group. Prior investigators have reported a 0.3 kg difference between mean TBW values determined by $^{18}$O-labeled water H$_2$O) from urine samples. In addition, these investigators showed that TBW measurements from saliva samples were equivalent to those measured from urine samples. This difference was within the expected measurement error (precision of <1%) of either method used in this study. It was assumed that the bromide space of the subjects in the development and validity groups represented the ECW.

After an overnight fast, subjects reported to the Exercise Physiology Laboratory at the Johnson Space Center in the morning for collection of baseline saliva (development group) or urine (validity group) samples. They then ingested a dose of water containing 40 g of 10.6 atom percent H$_2$$^{18}$O or 4 g of 99.8 atom percent $^2$H$_2$O (Icon Services, Summit, N.J.) diluted to 100 g total volume with tap water. Samples collected 3, 4, and 5 h after administration of the dose were stored frozen in cryogenically stable tubes at −20° C. until analysis. Samples were prepared according to the procedures for $^{18}$O/$^{16}$O or $^2$H/$^1$H isotope-ratio measurements by gas-isotope-ratio mass spectrometry.

Dilution space was calculated from baseline, 4-h, and 5-h sample collections by using the following equation:

$$N(mol) = ((W \cdot A)/18.02 \cdot a)) \cdot ((\delta a - \delta t)/(\delta s - \delta p))$$

were N is the pool space; W is the amount of water used to dilute the dose; A is the amount of dose administered; a is the dose diluted for analysis; and δ is enrichment of dose A, tap water t, peak postdose sample s, and predose baseline sample p. To account for incorporation of tracer into non-aqueous tissue, a correction factor of 1.04 (deuterium) or 1.01 ($^{18}$O-labeled water) was used for the relationship between the isotope dilution space and TBW. The estimated error of the laboratory for this measurement is <1% (based on the difference between 4- and 5-h samples).

It was assumed that ECW was the bromide dilution space. Baseline bromide levels were determined from an initial blood sample. Subjects then ingested an oral dose of bromide (1.2 g of NaBr). Additional blood samples were collected 3 and 4 h after administration of the dose. All samples were centrifuged, and the plasma was stored at −20° C. Plasma proteins were removed from the sample before ion chromatography by adding 0.3 mL of the sample to Ultra-free-PF Filter units (10,000 nominal mol mass limit; Millipore, Bedford, Mass.). Pressurizing the filter assembly with 10 mL of air from a plastic syringe activated the units. The protein-free filtrate (60 μL) was diluted 1:100 with ion chromatography eluant (1.8 mM Na$_2$CO$_3$/1.7 mM NaHCO$_3$). Recovery of bromide-spiked plasma samples was >90%.

Bromide concentration in the samples was determined by using ion chromatography (Dionex model 2000i suppression-based system; Dionex, Sunnyvale, Calif.). Samples (500 μL) were automatically injected onto the AS4A column (Dionex) by using the Dionex autosampler module with a flow rate set at 1 ml/min. Bromide was determined by suppression-based conductivity detection and quantified by using a calibration curve (least squares linear regression).

ECW volumes were determined from the difference in plasma bromide concentrations between the baseline and 3-h samples. ECW was calculated as follows:

$$ECW = Br_{dose}/[Br] \cdot 0.90 \cdot 0.95 \cdot 0.94$$

where Br$_{dose}$ was the amount of bromide orally administered to the subject, [Br] was the plasma bromide concentration obtained from the difference between the 0- and 3-h blood samples, 0.90 was the fraction of the bromide assumed to be extracellular, 0.95 was the Donnan equilibrium factor, and 0.94 was the assumed water content of plasma.

Impedance and resistance were measured using the embodiment of FIG. 4. The impedance analyzer 12, may be a Hewlett-Packard model 4284A Precision LCR Meter. Electrodes 10 were placed on the hand, wrist, ankle, and foot at standard locations before subjects 11 assumed the supine position. An input signal of 250 μA at frequencies of 5, 50, 67, 85, 100, 150, 166, 200, 250, and 300 kHz was applied. Subjects 11 reclined to a supine position, and a data acquisition unit 13, which may be a computer, recorded the impedance and resistance immediately and after 40 minutes of quiet rest. A blanket or extra clothing kept the subjects warm during the rest period and reduced possible variation in impedance and resistance caused by skin temperature changes. The difference between the impedance and resistance measured at 0 and 40 minutes evaluated the effects of shifting fluids between interstitial and vascular spaces. Prior investigators showed an association between the increases in total body resistance RT (measured at a set frequency) and decreases in hematocrit that accompany a change in posture.

Determination of circuit components of the human body circuit model was made according to the body circuit model of FIG. 5. The determination of circuit components used the 1% impedance method illustrated by FIG. 6 instead of the Cole—Cole method used by prior investigators. The results of the 1% impedance method produced resistances similar to graphic techniques based on the Cole—Cole method. Each subject's impedance and resistance were regressed versus frequency using 3rd-order least square regression. Referring to FIG. 6, the extra-cellular resistor RE was the resistance at a frequency of 0 Hz. At a frequency of 0 Hz, the current preferentially flows through the extra-cellular side of the circuit because the capacitor acts as a gap on the intra-cellular side of the circuit. The resistance of the total circuit RT was the resistance at the frequency where impedance changed by only 1% with a frequency increase of 25 kHz.

The 1% limit was used because it is an industry standard for high-precision resistors. Impedance was used because it incorporated resistance, capacitance, and inductance. The 25 kHz frequency increment was previously shown to be sufficient to identify the 1% impedance. This analytical approach uses the theory that, at very low frequencies, the electrical current does not enter cells, whereas at high frequencies, the current enters both the intracellular and extracellular fluid spaces. The intra-cellular resistor $R_I$ is the difference between one divided by the $R_T$ and one divided by $R_E$.

The method of determining circuit components illustrated by FIG. 6 discussed above is a teleological approach and is different from the traditional Cole—Cole method. The Cole—Cole method solves for resistances when reactance is zero. The Xitron BIS 4000B analyzer (Xitron Technologies, San Diego, Calif.) uses a modified Cole—Cole approach with iterative curve fitting. Unlike the Cole—Cole method, the modified Cole—Cole method allows for the removal of 25% of the data to increase the fit of the resistance and reactance values. The method of the present invention uses all the data. A high correlation (r=0.987–0.994) was observed between the analysis techniques for the $R_E$ and $R_T$ resistors. However, the main predictor of TBW, $Ht^2/R_T$, had a significantly weaker correlation and larger standard error of the estimate (SEE; r=0.693±5.6 kg) for the Cole—Cole analysis than that observed from present invention (r=0.945±2.6 kg).

Stepwise multiple regression equations to calculate TBW and ECW were developed from the $R_T$ and $R_E$ values of the human body circuit model. The TBW equation used $Ht^2/R_T$ and body mass m, whereas ECW only used $Ht^2/R_E$. The validity of these equations were evaluated with four statistical tests: mean differences (analysis of variance, Newman-Keuls post hoc testing), strength of linear relationship (Pearson product-moment correlations), SEE, and Bland-Altman pairwise comparisons. These statistical tests are standard statistical methods known to one having ordinary skill in the art.

The Bland-Altman pairwise comparison evaluates the validity of a new method to an accepted technique. This comparison was a graphical representation of the difference (absolute or % Δ from accepted method) between methods and the average of these methods. Bland-Altman suggests that if all values are within ±2 SD (standard deviation) of the averaged values and there is no correlation between the differences versus the averaged values, then the methods are clinically equivalent. Validity of a new method decreases if the mean difference is greater than the measurement error, the Bland-Altman plot shows date points outside confidence intervals, and there is a significant relationship indicating that one method overestimates or underestimates the other as a function of size.

The stepwise multiple regression for TBW yielded the following equation for TBW with a multiple R of 0.987 and SEE of 1.26 kg:

$$TBW(kg)=2.584+0.379 \cdot Ht^2/R_T+0.1686 \cdot m$$

where $R_T$ is the resistance (ohms) of the circuit and m is the body mass (kg). The mean ± SD of $R_T$ for the development group was 465±83 ohms. The stepwise multiple regression for ECW yielded the following equation for ECW with a multiple R of 0.858 and SEE of 1.72 kg:

$$ECW(kg)=2.854+0.2877 \cdot Ht^2/R_E$$

where $R_E$ is the resistance (ohms) of the circuit at a frequency of 0 Hz. The mean ± SD of $R_E$ for the development group was 683±88 ohms. No other independent variables (age or gender) significantly improved the strength of the ECW equation.

Figure 8:
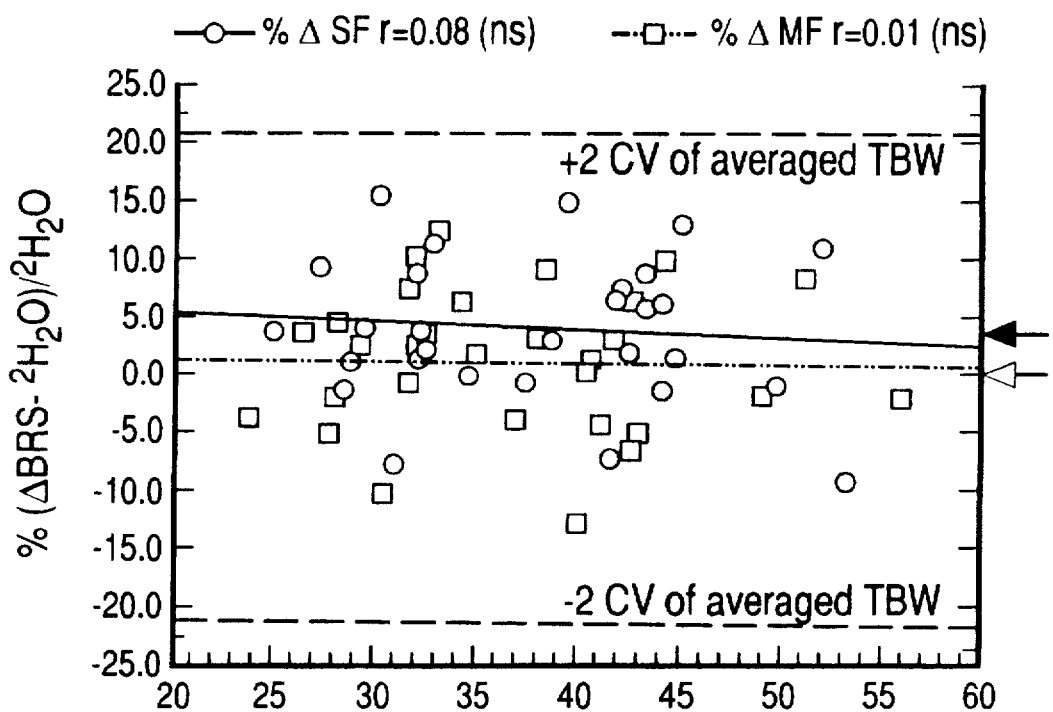
FIG. 8 illustrates a Bland-Altman plot of the total body water calculations of the present invention versus a prior art method.

The TBW and ECW calculations were evaluated for validity. TBW had high correlations (r=0.956–0.964) and low SEE (2.08–2.28 kg) compared with results obtained using isotopic dilution in the validity group. The calculation of TBW was not significantly different from the dilution values for both 0 and 40 minutes (1.3±6.1 and −0.4±5.5% for 0 and 40 min, respectively). Referring to FIG. 8 and Table 2, the Bland-Altman correlations for % change (BRS-dilution) versus averaged TBW were not significantly different from zero. FIG. 8, shows a Bland-Altman plot for a single-frequency prior art BRS method (SF) and the multi-frequency BRS method of the present invention (MF) versus dilution at 0 minutes. The solid arrow indicates the mean difference for the SF method versus dilution, and the open arrow indicates the mean difference for the present invention versus dilution. This indicated there is no trend in the calculations for TBW. Values for the TBW calculations were within 2 SD of the averaged values. For details of the SF method, see *Estimation of Total Body Water by Bioelectrical Impedance Analysis*, R. F. Kushner and D. A. Schoeller, American Journal of Clinical Nutrition, vol. 44 pages 417–424, 1986.

Figure 9:
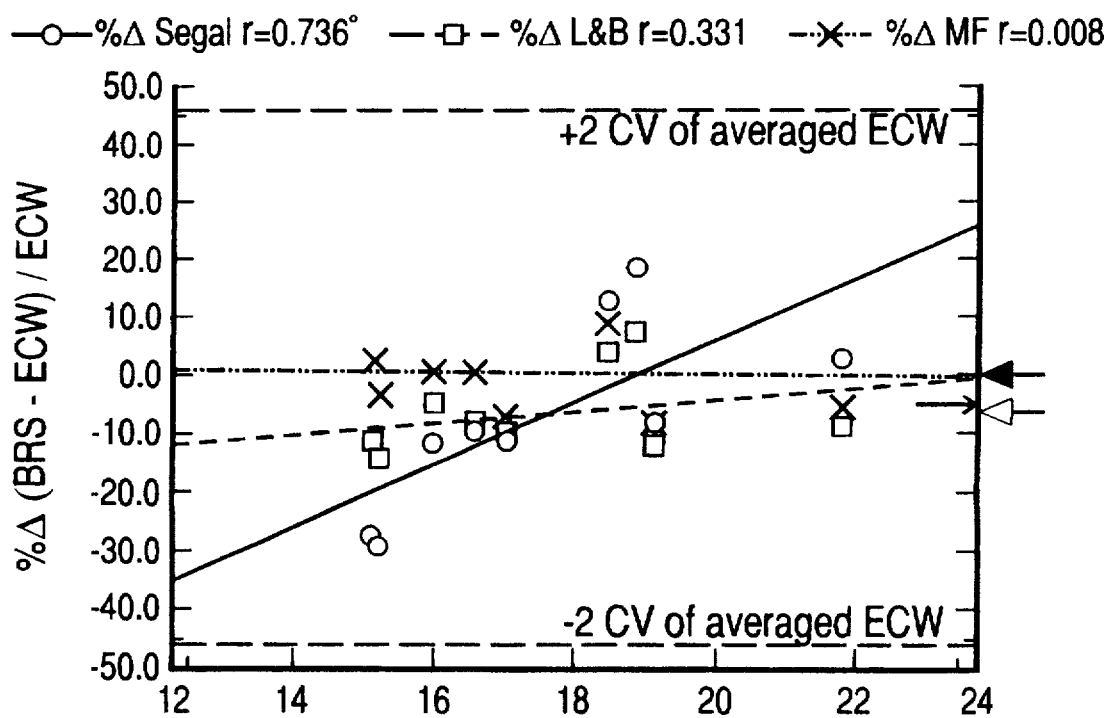
FIG. 9 illustrates a Bland-Altman plot of the extra-cellular water calculations of the present invention versus a prior art method.

The calculations for ECW had high correlations (r=0.941–0.949) and low SEE (1.27–1.12 kg) compared with results obtained using dilution in the validity group. Referring to Table 2, the calculations for ECW were not significantly different from dilution at both 0 and 40 minutes (1.2±7.7 and −1.7±7.6%, respectively). Referring to FIG. 9 and Table 2, the Bland-Altman correlations for % A (BRS -dilution) versus averaged ECW were not significantly different from zero at 0 or 40 minutes. FIG. 9 shows a Bland-Altman plot for two prior art BRS methods, Segal et al (Segal) and Lukaski and Bolonchuk (L&B), and the multi-frequency BRS method of the present invention (MF) versus dilution at 0 minutes. The open and solid arrows indicate the mean differences for the L&B and Segal BRS methods versus dilution, and the plain arrow indicates the mean difference for the present invention versus dilution. This indicated there was no trend in the calculations for ECW. Values for the TBW calculations were within 2 SD of the averaged values. For details of the L&B and Segal BRS methods, see *Estimation of Body Fluid Volumes Using Tetrapolar Biolectrical Impedance Measurements*, H. C. Lukaski and W. W. Bolonchuk, Aviation Space and Environmental Medicine, vol. 59 pages 1163–1169, 1988; *Estimation of Extracullar and Total Body Water by Multiple-frequency Bioelectrical-Impedance Measurement*, K. R. Segal, S. Burastero, A. Chun, P. Coronel, R. N. Pearson, Jr., and J. Wang, American Journal of Clinical Nutrition, vol. 54 pages 26–29, 1991.

Equations were developed for calculating TBW and ECW from the circuit components of the human body circuit model. The calculations for TBW and ECW were not affected by fluid shifts that occur after 40 min of supine rest. These calculations have good statistical validity, based on the strength of the correlations (r=0.941–0.969), low SEE (1.15–2.28 kg), nonsignificant mean differences (BRS-dilution; % change=−0.4 to 1.3%) that were close to the expected measurement errors for TBW (±1%) and ECW (±5%), and Bland-Altman pairwise comparisons that showed no significant trend.

TABLE 2

TBW and ECW Validation Results

|  | Mins | Dilution (kg) | BRS (kg) | Dilution vs. BRS | | | Bland-Altman | |
|---|---|---|---|---|---|---|---|---|
|  |  |  |  | r | SEE (kg) | r | % Δ (mean) | SD (%) |
| TBW (n = 31) |  | 36.55 ± 7.83 |  |  |  |  |  |  |
| BRS | 0 |  | 37.22 ± 7.80 | 0.956 | 2.28 | 0.013 | 1.3 | 6.1 |
| BRS | 40 |  | 36.42 ± 7.86 | 0.964 | 2.08 | −0.007 | −0.4 | 5.5 |
| ECW (n = 9) |  | 17.22 ± 4.30 |  |  |  |  |  |  |
| BRS | 0 |  | 16.93 ± 4.62 | 0.941 | 1.27 | −0.008 | 1.2 | 7.7 |
| BRS | 40 |  | 17.09 ± 5.08 | 0.949 | 1.12 | −0.073 | −1.7 | 7.6 |

In developing the equations to calculate total blood volume TBV and plasma volume PV, 19 subjects were in the development group and 10 subjects were in the validity group. For the 19 subjects (9 males and 10 females, age 34.6±5.7 yr, weight 65.5±13.2 kg, and height 171±11 cm) in the development group, impedance and resistance were assessed using the method of the present invention, and TBV and PV were assessed using dilution. For the 10 subjects (4 males and 6 females, age 34.1±7.5 yr, weight 73.9±14.7 kg, and height 170±8 cm) in the validity group, TBV and PV were assessed using dilution. The equations developed using the development group were then applied to the validity group, and the results thereof were compared to dilution results.

Impedance and resistance were measured using the embodiment of FIG. 4 discussed above in the explanation of the development of TBW and ECW equations. Subjects were reclined in a supine position and impedance and resistance were measured after 40 minutes.

Blood and plasma volume measurements were made using $^{125}$I-labeled albumin after subjects rested for at least 30 minutes in the supine position. Subjects ingested a small amount of concentrated, nonradioactive iodide solution (Lugol's solution, 200 mg iodide in ~50 mL) before isotope injection. This iodide solution saturated the thyroid gland to reduce the thyroidal radiation dose due to sequestering of $^{125}$I liberated from the catabolism of labeled albumin. Then the subjects were injected with a sample of human serum albumin labeled with 10 microcuries or less of $^{125}$I. Blood samples (10 mL per sample) were obtained before the injection, and at 10 and 20 minutes after the injection for analysis of radioactive iodine. Technical error was estimated to be less than 1% and biological variation was estimated to be less the 3%. Therefore, the estimated propagated error for the three blood samples is less than 5.2%. Plasma volume PV was calculated using back extrapolation of exponential clearance to zero time. Hematocrit was analyzed from the blood samples taken for plasma volume measurement. The hematocrit was multiplied by 0.87 to compensate for a difference between the body and peripheral venous hematocrit. Red cell volume was estimated from the plasma volume PV and hematocrit:

red cell volume=hematocrit·PV/(1-hematocrit). Total blood volume TBV was calculated by adding the plasma volume PV and the red cell volume.

Determination of circuit components of the human body circuit model was made using the method represented in FIG. 6 discussed above in the explanation of the development of TBW and ECW equations.

Results from the 19 subjects of the development group were evaluated for validity using four statistical tests: mean differences (dependent t-ratio, two-tail testing), strength of linear relationship (Pearson product-moment correlations), standard error of estimates (SEE), and Bland-Altman pair-wise comparison. Statistical power (1−β) was computed for the regression models and dependent t-tests. These statistical tests are standard statistical methods known to one having ordinary skill in the art.

Stepwise multiple regression analysis was used to develop models for total blood volume TBV and plasma volume PV for the 19 subjects in the development group using the human body circuit model. Prior investigators assumed total body resistance $R_T$ was due to total body water TBW and was equivalent to the resistance of a wire. The volume of the wire can be determined from the following equation:

$$volume = \rho \cdot length^2 / R$$

where ρ is the specific resistivity (ohms·cm) of the wire and R is the resistance. The length of the wire is generally the subject's height. However, strict application of this equation to assess blood volume using previously reported specific resistivity of blood is not possible because blood resistivity changed with hematocrit. The present invention used ratios of $Ht^2$ over different electrical components to avoid this problem. The equations for TBV and PV are as follow:

$$TBV(mL) = -868.9 + 1.048E - 5 \cdot (Ht^2/M) - 4.996 \cdot (Ht^2/R_E) + 3.489E7 \cdot M$$

with multiple r=0.915, SEE=358 mL (8.8%), F-ratio (3, 18 df)=25.65, power (1−β)=99%; and $$PV(mL) = -1649 + 4.941E - 6 \cdot (Ht^2/L) + 4.309E7 \cdot L - 9.014E6 \cdot M$$

with multiple r=0.903, SEE=233 mL (8.9%), F-ratio (3, 18 df)=22.08, power (1−β)=99%.

Total blood volume TBV and plasma volume PV for these 19 subjects measured using dilution were 4045±809 mL and 2605±494 mL, respectively.

The equations for total blood volume TBV and plasma volume PV were then applied to the 10 subjects of the second group. Table 3 shows the TBV and PV results for the 10 subjects in the validation group. The TBV and PV results obtained using the equations and using dilution for these 10 subjects were not statistically different (P>0.05). The differences were less than the estimated propagated error of ±5.2%.

Figure 10:
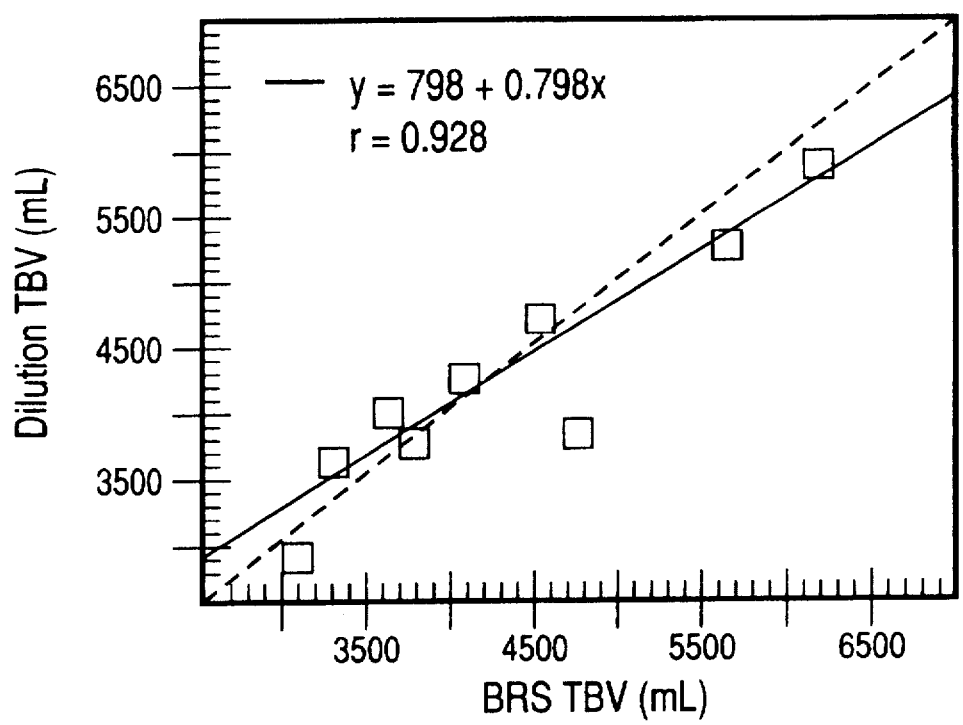
FIG. 10 illustrates Pearson product-moment correlations between total blood volume calculations of the present invention versus a prior art method.
Figure 11:
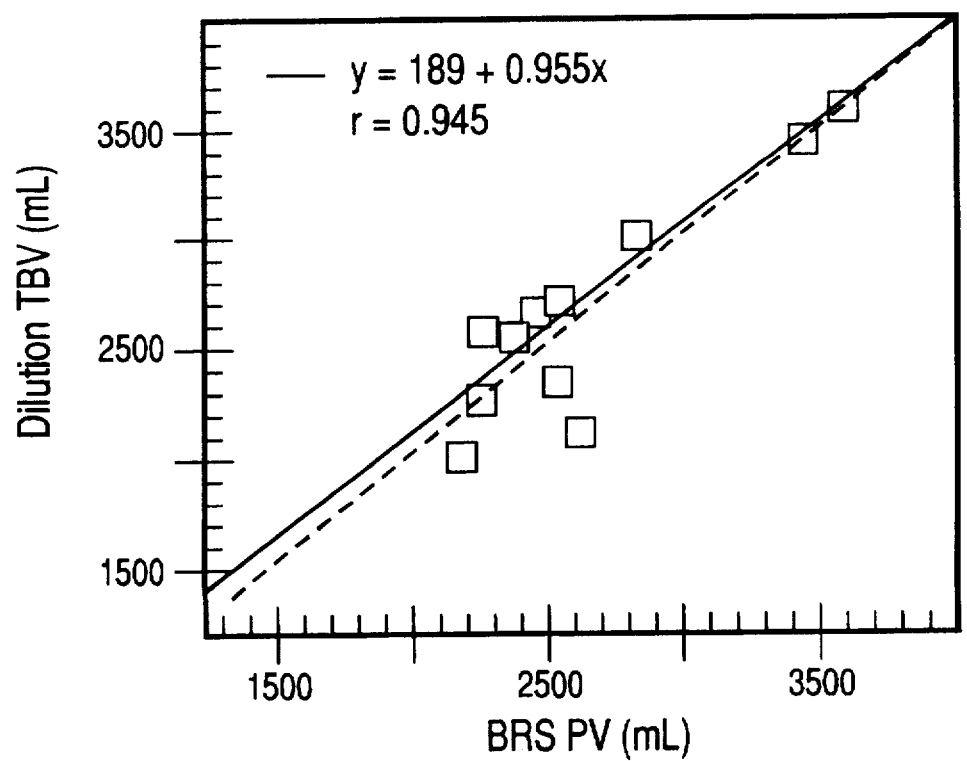
FIG. 11 illustrates Pearson product-moment correlations between plasma volume calculations of the present invention versus a prior art method.

Referring to FIG. 10, Pearson product-moment correlations between TBV calculations and dilution is shown (r=0.298). Dashed line represents the method of the present invention, solid line represents dilution. Referring to FIG. 11, Pearson product-moment correlations between PV calculations and dilution is shown (r=0.945). Dashed line represents the method of the present invention, solid line represents dilution. These relationships were significantly different from zero (P<0.005), and SEE was low for both TBV (7.7%) and PV (6.1%) when expressed as a percentage of mean dilution values.

Figure 12:
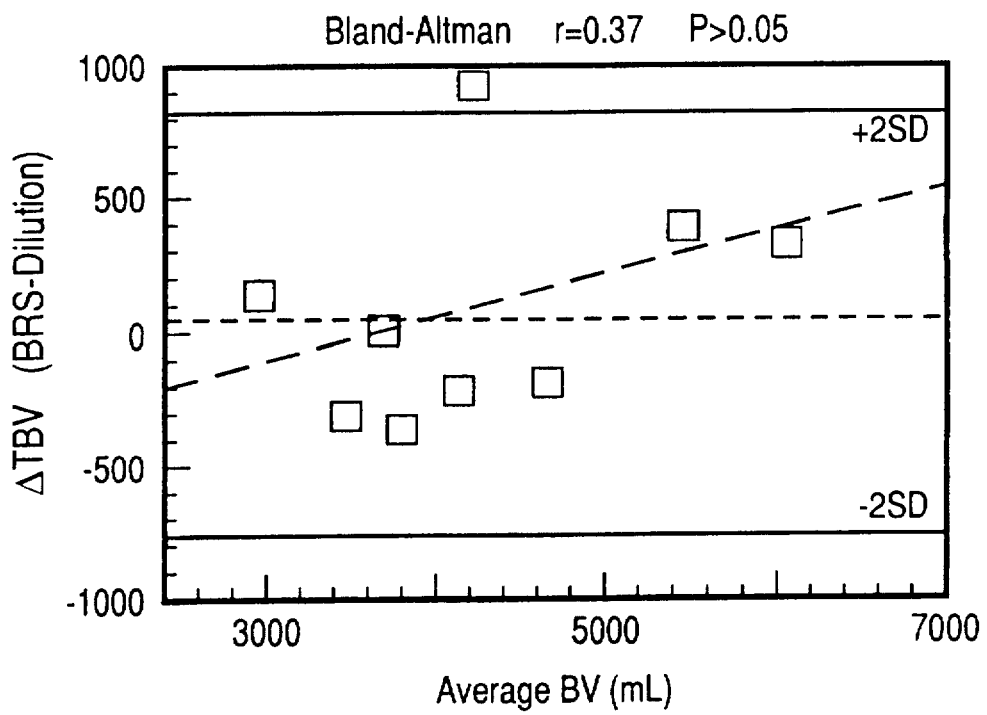
FIG. 12 illustrates a Bland-Altman plot of the total blood volume calculations of the present invention versus a prior art method.
Figure 13:
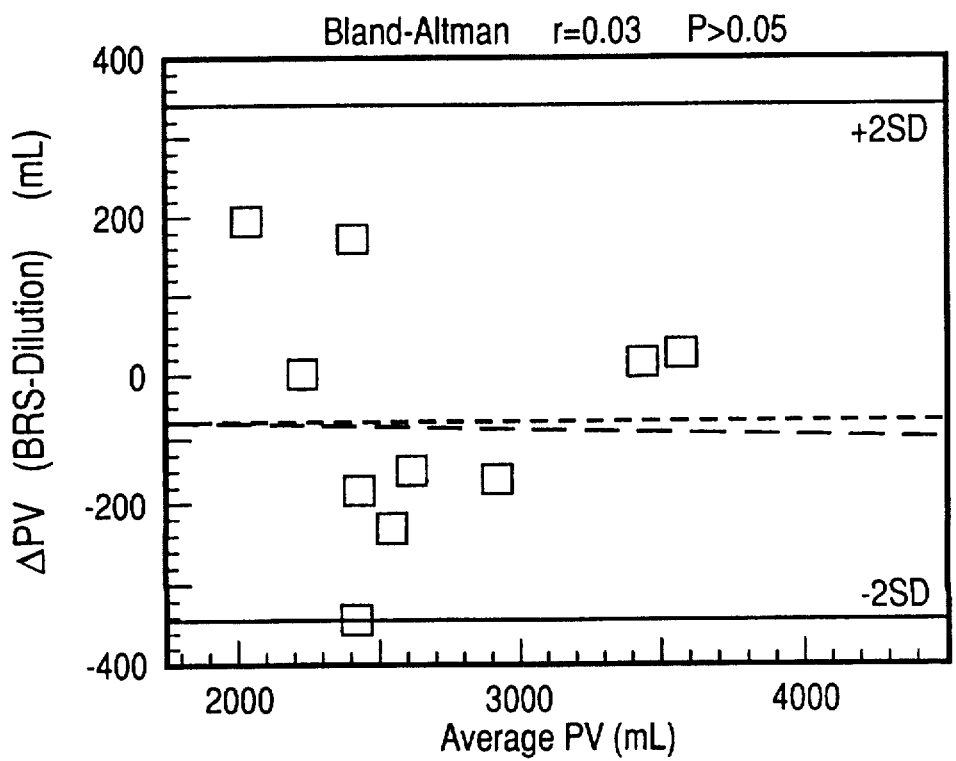
FIG. 13 illustrates a Bland-Altman plot of the plasma volume calculations of the present invention versus a prior art method.

Referring to FIG. 12, a Bland-Altman pairwise comparisons plot is shown for TBV. The short dashed line is the mean difference of 67 mL. The long dashed line is the regression line of the difference versus averaged values of the present invention versus dilution. Referring to FIG. 13, a Bland-Altman pairwise comparisons plot is shown for TBV. The short dashed line is the mean difference of −69 mL. The long dashed line is the regression line of the difference versus averaged values of the present invention versus dilution. Both comparisons show all differences except one are within ±2 SD of averaged values and there are no significant relationships that indicate one method over- or underestimates the other as a function of size. These results show the equations developed are statistically valid for assessing total blood volume TBV and plasma volume PV.

TABLE 3

TBV and PV Validity Results

|  | Total Blood Volume | Plasma Volume |
| --- | --- | --- |
| r (Dilution vs BRS) | 0.928 | 0.945 |
| SEE (mL) | 327 | 167 |
| SEE (%) | 7.7 | 6.1 |
| % Change | 1.5 ± 9.7 | −2.3 ± 6.9 |
| BRS | 4293 ± 805 | 2657 ± 503 |
| Dilution | 4227 ± 878 | 2725 ± 508 |
| Power (1 − β) at α ± 0.05 | 96% | 94% |

It should be noted that the studies described above used a limited number of test subjects. Notwithstanding the limited number of test subjects, the equations developed accurately determined total body water TBW, extra-cellular water ECW, total blood volume TBV, and plasma volume PV.

It is to be understood that the embodiments described above is merely illustrative of some of the many specific embodiments of the present invention, and that other arrangements can be devised by one of ordinary skill in the art at the time the invention was made without departing from the scope of the invention.

What is claimed is:

1. A process for determining a volume of whole body fluid in a subject, comprising the steps of:

applying a signal to a subject;

increasing a frequency of the signal by predetermined increments;

measuring an impedance and a resistance of the subject at each frequency increment;

determining a total body frequency $F_T$, wherein the total body frequency $F_T$ is the frequency at which the impedance decreases by a predefined percent over a predefined frequency interval;

determining circuit components of a human body circuit model, wherein the circuit components comprise a total body impedance $Z_T$, a total body resistance $R_T$, an extra-cellular resistance $R_E$, an intra-cellular resistance $R_I$, a capacitance C, a self-inductance L, and a mutual-inductance M; and determining the volume of whole body fluid from the circuit components.

2. The process of claim 1, wherein the step of applying a signal to a subject comprises an alternating, low amperage square wave.

3. The process of claim 1, wherein the step of increasing a frequency of the signal by predetermined increments comprises increasing the frequency from 0 kHz to 300 kHz.

4. The process of claim 3, wherein the step of increasing a frequency of the signal by predetermined increments comprises ten predetermined frequency increments.

5. The process of claim 3, wherein the step of increasing a frequency of the signal by predetermined increments comprises a maximum frequency of no more than 300 kHz.

6. The process of claim 1, wherein the step of determining a total body frequency $F_T$ comprises a predefined percent of impedance decrease of no more than 1%.

7. The process of claim 6, wherein the step of determining a total body frequency $F_T$ comprises a predefined frequency interval of 25 kHz.

8. The process of claim 1, wherein the step of determining circuit components of a human body circuit model comprises a human body circuit model having a first resistor in series with a capacitor, a second resistor in series with two parallel inductors, and the first resistor and capacitor are in parallel with the second resistor and two parallel inductors.

9. The process of claim 8, wherein the step of determining circuit components of a human body circuit comprises determining a negative mutual-inductance M.

10. The process of claim 9, wherein the step of determining the volume of whole body fluid from the circuit comprises calculating an amount of total body water TBW using the total body resistance $R_T$, a subject's height Ht and body mass m in the following equation:

$$TBW(kg)=2.584+0.379 \cdot (Ht^2/R_T)+0.168 \cdot m.$$

11. The process of claim 9, wherein the step of determining the volume of whole body fluid from the circuit components comprises calculating an amount of extra-cellular water ECW using the extra-cellular resistance $R_E$ and a subject's height Ht in the following equation:

$$ECW(kg)=2.854+0.2877 \cdot (Ht^2/R_E).$$

12. The process of claim 9, wherein the step of determining the volume of whole body fluid from the circuit components comprises calculating a total blood volume TBV using the negative mutual-inductance M, the extra-cellular resistance $R_E$, and a subject's height Ht in the following equation:

$$TBV(mL)=-868.9+1.048E-5 \cdot (Ht^2/M)-4.996 \cdot (Ht^2/R_E)+3.489E7 \cdot M.$$

13. The process of claim 9, wherein the step of determining the volume of whole body fluid from the circuit components comprises calculating a plasma volume PV using the self-inductance L, the negative mutual-inductance M, and a subject's height Ht in the following equation:

$$PV(mL)=-1649+4.941E-6 \cdot (Ht^2/L)+4.309E7 \cdot L-9.014E6 \cdot M.$$

14. An apparatus for determining a volume of whole body fluid in a subject, comprising of:

means for applying a signal to a subject;

means for increasing a frequency of the signal by predetermined increments;

means for measuring an impedance and a resistance of the subject at each frequency increment;

means for determining a total body frequency $F_T$, wherein the total body frequency $F_T$ is the frequency at which the impedance decreases by a predefined percent over a predefined frequency interval;

means for determining circuit components of a human body circuit model, wherein the circuit components comprise a total body impedance $Z_T$, a total body resistance R$_T$, an extra-cellular resistance R$_E$, an intra-cellular resistance R$_I$, a capacitance C, a self-inductance L, and a mutual-inductance M; and means for determining the volume of whole body fluid from the circuit components.

15. The apparatus of claim 14, wherein the means for applying a signal to a subject comprises a means for applying an alternating, low amperage square wave.

16. The apparatus of claim 14, wherein the means for increasing a frequency of the signal by predetermined increments comprises a means for increasing the frequency from 0 kHz to 300 kHz.

17. The apparatus of claim 16, wherein the means for increasing a frequency of the signal by predetermined increments comprises ten predetermined frequency increments.

18. The apparatus of claim 16, wherein the means for increasing a frequency of the signal by predetermined increments comprises a maximum frequency of no more than 300 kHz.

19. The apparatus of claim 14, wherein the means for determining a total body frequency F$_T$ comprises a predefined percent of impedance decrease of no more than 1%.

20. The apparatus of claim 19, wherein the means for determining a total body frequency F$_T$ comprises a predefined frequency interval of 25 kHz.

21. The apparatus of claim 14, wherein the means for determining circuit components of a human body circuit model comprises a human body circuit model having a first resistor in series with a capacitor, a second resistor in series with two parallel inductors, and the first resistor and capacitor are in parallel with the second resistor and two parallel inductors.

22. The apparatus of claim 21, wherein the means for determining circuit components of a human body circuit comprises a means for determining a negative mutual-inductance M.

23. The apparatus of claim 22, wherein the means for determining the volume of whole body fluid from the circuit comprises a means for calculating an amount of total body water TBW using the total body resistance R$_T$, a subject's height Ht and body mass m in the following equation:

$$TBW(kg) = 2.584 + 0.379 \cdot (Ht^2/R_T) + 0.168 \cdot m.$$

24. The apparatus of claim 22, wherein the means for determining the volume of whole body fluid from the circuit components comprises a means for calculating an amount of extra-cellular water ECW using the extra-cellular resistance R$_E$ and a subject's height Ht in the following equation:

$$ECW(kg) = 2.854 + 0.2877 \cdot (Ht^2/R_E).$$

25. The apparatus of claim 22, wherein the means for determining the volume of whole body fluid from the circuit components comprises a means for calculating a total blood volume TBV using the negative mutual-inductance M, the extra-cellular resistance R$_E$, and a subject's height Ht in the following equation:

$$TBV(mL) = -868.9 + 1.048E\text{-}5 \cdot (Ht^2/M) - 4.996 \cdot (Ht^2/R_E) + 3.489E7 \cdot M.$$

26. The apparatus of claim 22, wherein the means for determining the volume of whole body fluid from the circuit components comprises a means for calculating a plasma volume PV using the self-inductance L, the negative mutual-inductance M, and a subject's height Ht in the following equation:

$$PV(mL) = -1649 + 4.941E\text{-}6 \cdot (Ht^2/L) + 4.309E7 \cdot L - 9.014E6 \cdot M.$$

27. An apparatus for determining a volume of whole body fluid in a subject, comprising:

a signal generator configured to apply a signal to a subject and to increase a frequency of the signal by predetermined increments;

an impedance analyzer configured to measure an impedance and a resistance of the subject at each frequency increment; and a data processing unit configured to determine a total body frequency F$_T$ where the impedance decreases by a predefined percent over a predefined frequency interval, determine circuit components of a human body circuit model including a total body impedance Z$_T$, a total body resistance R$_T$, an extra-cellular resistance R$_E$, an intra-cellular resistance R$_I$, a capacitance C, a self-inductance L, and a mutual-inductance M, and determine the volume of body fluid from the circuit components.

28. The apparatus of claim 27, wherein the signal comprises an alternating, low amperage square wave.

29. The apparatus of claim 27, wherein the frequency of the signal comprises a frequency range of 0 kHz to 300 kHz.

30. The apparatus of claim 29, wherein the predetermined increments comprise ten predetermined increments.

31. The apparatus of claim 29, wherein the frequency of the signal comprises a maximum frequency of no more than 300 kHz.

32. The apparatus of claim 27, wherein the predefined percent of impedance decrease comprises a decrease of no more than 1%.

33. The apparatus of claim 32, wherein the predefined frequency interval comprises an interval of 25 kHz.

34. The apparatus of claim 27, wherein the human body circuit model comprises a human body circuit model having a first resistor in series with a capacitor, a second resistor in series with two parallel inductors, and the first resistor and capacitor are in parallel with the second resistor and two parallel inductors.

35. The apparatus of claim 34, wherein the circuit components of the human body circuit model comprises a negative mutual-inductance M.

36. The apparatus of claim 35, wherein the volume of whole body fluid comprises an amount of total body water TBW which may be calculated using the total body resistance R$_T$, a subject's height Ht and body mass m in the following equation:

$$TBW(kg) = 2.584 + 0.379 \cdot (Ht^2/R_T) + 0.168 \cdot m.$$

37. The apparatus of claim 35, wherein the volume of whole body fluid comprises an amount of extra-cellular water ECW which may be calculated using the extra-cellular resistance R$_E$ and a subject's height Ht in the following equation:

$$ECW(kg) = 2.854 + 0.2877 \cdot (Ht^2/R_E).$$

38. The apparatus of claim 35, wherein the volume of whole body fluid comprises a total blood volume TBV which may be calculated using the negative mutual-inductance M, the extra-cellular resistance R$_E$, and a subject's height Ht in the following equation:

$$TBV(mL) = -868.9 + 1.048E\text{-}5 \cdot (Ht^2/M) - 4.996 \cdot (Ht^2/R_E) + 3.489E7 \cdot M.$$

39. The apparatus of claim 35, wherein the volume of whole body fluid comprises a plasma volume PV which may be calculated using the self-inductance L, the negative mutual-inductance M, and a subject's height Ht in the following equation:

$$PV(mL) = -1649 + 4.941E\text{-}6 \cdot (Ht^2/L) + 4.309E7 \cdot L - 9.014E6 \cdot M.$$

* * * * *